US006920792B2

(12) United States Patent
Flora et al.

(10) Patent No.: US 6,920,792 B2
(45) Date of Patent: Jul. 26, 2005

(54) TRANSDUCER GUIDED WAVE ELECTROMAGNETIC ACOUSTIC

(76) Inventors: John H. Flora, 5108 Wedgewood Rd., Lynchburg, VA (US) 24503; Charles M. Fields, 258 Munford St., Lynchburg, VA (US) 24501; Daniel P. Geier, 1199 Summerpark Dr., Forest, VA (US) 24551

(*) Notice: Subject to any disclaimer, the term of this patent is extended or adjusted under 35 U.S.C. 154(b) by 22 days.

(21) Appl. No.: 10/429,375

(22) Filed: May 5, 2003

(65) Prior Publication Data

US 2004/0221652 A1 Nov. 11, 2004

(51) Int. Cl.[7] .............................................. G01N 29/00
(52) U.S. Cl. ........................................ 73/622; 73/643
(58) Field of Search ......................... 73/643, 597, 598, 73/599, 600, 622, 632

(56) References Cited

U.S. PATENT DOCUMENTS

| 4,184,374 A | * | 1/1980 | Thompson et al. ........... 73/640 |
| 4,471,658 A | * | 9/1984 | Morimoto ..................... 73/643 |
| 4,793,185 A | * | 12/1988 | Boettger et al. .............. 73/643 |
| 5,359,898 A | * | 11/1994 | Latimer ....................... 73/600 |
| 5,456,113 A | * | 10/1995 | Kwun et al. .................. 73/587 |
| 5,581,037 A | * | 12/1996 | Kwun et al. .................. 73/623 |
| 5,619,423 A | * | 4/1997 | Scrantz ........................ 702/51 |
| 5,811,682 A | * | 9/1998 | Ohtani et al. ................ 73/643 |
| 5,866,820 A | * | 2/1999 | Camplin et al. .............. 73/643 |
| 5,907,100 A | * | 5/1999 | Cook ........................... 73/602 |
| 6,148,672 A | * | 11/2000 | Cawley et al. ............... 73/622 |
| 6,164,137 A | * | 12/2000 | Hancock et al. ............. 73/643 |
| 6,170,336 B1 | * | 1/2001 | Johnson et al. .............. 73/643 |
| 6,443,011 B1 | * | 9/2002 | Schulze et al. .............. 73/622 |
| 2002/0092353 A1 | * | 7/2002 | Passarelli, Jr. ............... 73/643 |

FOREIGN PATENT DOCUMENTS

JP 61107154 A * 5/1986 .......... G01N/29/04

* cited by examiner

Primary Examiner—Hezron Williams
Assistant Examiner—Rose M. Miller
(74) Attorney, Agent, or Firm—James W. Hiney (57) ABSTRACT

A guided wave electromagnetic acoustic transducer for detecting defects in moving metallic products such as rods, tubes and the like and which has coils energized by pulse of a few cycles of a high frequency alternating voltage which produces an alternating field in the product, the coils being alternately wound and connected in series and measuring dynamic acoustic stress that is a function of the radial distance from the center of the product being tested and produces a reading that is different than that showing a surface defect in the product.

36 Claims, 10 Drawing Sheets

TRANSDUCER GUIDED WAVE ELECTROMAGNETIC ACOUSTIC

The present invention relates to electromagnetic acoustic transducers in general and more specifically to an electromagnetic acoustic design which provides for the transmission and reception of guided acoustic waves in metallic rods, bars, wire and tubes for the purpose of detection of defects therein and for measuring certain properties of these metal products during and after their fabrication.

BACKGROUND

Electromagnetic Acoustic Transducers (EMATs) are electrical devices that can transmit and receive ultrasonic sound waves in an electrically conducting material without requiring contact of the probe with the material being inspected. EMATs are typically composed of arrays of electrical conductors, commonly referred to as coils and magnets, which can either be permanent magnets or electromagnets. When the electrical conductors comprising the arrays are energized by an alternating electrical current and placed in close proximity to an electrically conducting material, eddy currents are induced in the material. When these eddy currents are induced in the presence of a magnetic field, forces known as Lorentz forces are applied to the transient electrons of the induced eddy currents. A Lorentz force (F) at a point in the material is described mathematically by the cross product of the magnetic flux density (B), the induced eddy current density (J) and the relationship therebetween is shown in the following equation.

$$F = J \times B$$

The sum of these Lorentz forces produce an acoustic stress wave having the same frequency with respect to time as the induced eddy currents. The various types and modes of the waves which can be generated by EMATs are determined primarily by the configuration of the magnet, the configuration of the electrical conductors and their physical position with respect to each other. Guided waves such as the well known Lamb wave modes are easily generated in metal plates and cylinders by EMATs. These guided waves are generated near the surface of a section of the plate which is in close proximity to the EMAT and are transmitted from the EMAT in at least on direction within the material. Guided waves traveling under an EMAT are detected by the reverse process by causing the magnetic field under a conductor to change at the same frequency as the acoustic wave. As this alternating field is coupled to the electrical conductors of the EMAT coil, a signal voltage will be detected at the terminals of the coil as the acoustic wave travels under the EMAT.

EMATs offer several advantages when compared to piezoelectric transducers. EMATs do not require any fluid coupling for one and the acoustic waves that are generated are generated immediately below the surface of the material being tested unlike piezoelectric transducers in which the sound is produced in the probe and transferred to the material through a coupling medium such as oil or water. The latter characteristic provides substantially greater accuracy, reliability and repeatability for applications in which the test material is contaminated, rough, hot or moving at high speeds relative to the transducer. As EMAT fabrication can be very precise, components such as a sensor coil and/or a magnet or, even the entire EMAT, can be interchanged with little or no variation in acoustic beam shape and signal response to defects and/or to the material characteristics being detected or measured. Another advantage of the basic EMAT is its inherent simplicity of construction provides an almost unlimited variety of designs to implement shaping, steering and focusing acoustic beams to achieve the desired effect.

A further advantage of EMATs is their ability to generate guided waves in uniform metal components such as rods, plates and pipe. There are two basic types of guided waves, Lamb waves and horizontally polarized shear waves. Lamb waves are produced by the interaction of alternating magnetic fields with relatively constant magnetic fields at the surface of a metal component. The horizontally polarized shear waves are usually generated in ferromagnetic materials such as carbon steel and steel alloys which have the property of magnetostriction but can be generated through the interaction of magnetic fields which alternate in space but are constant in time with magnetic fields which are constant in space but alternate in time. The focus of this patent is the generation of Lamb waves in ferromagnetic and nonferromagnetic metal components which have a central axis symmetry.

THE PRIOR ART

There have been various EMAT configurations patented over the years. One such configuration is shown in U.S. Pat. No. 6,164,137 to Hancock et al. It shows a testing device for testing tubes for surface defects and displaying the results via an EMAT transmitter arranged collinear with a pair of EMAT receivers. This configuration is very different from the arrangements contemplated in the instant invention.

Cawley et al, in U.S. Pat. No. 6,148,672 disclose an arrangement for using Lamb waves to inspect elongate pipes and the like. This arrangement cannot be used to inspect defects in the central axis where the core is moving at high speed.

U.S. Pat. No. 6,443,011, discloses a device for detecting faults or measuring wall thicknesses of a continuously moving strip, section or tubes of plastic, using ultrasonic signals.

Latimer discloses, in U.S. Pat. No. 5,359,898, a method of checking for hydrogen damage in a boiler tube which includes a pair of electromagnetic acoustic coils which are mounted for movement to and away from one another but does not show segmented magnets and flexible coils. Latimer is one of the inventors in U.S. Pat. No. 5,085,082 which is used to detect flaws in welded pipes and the like. EMATS are employed to generate ultrasonic acoustic surface and shear waves.

Camplin et al show, in U.S. Pat. No. 5,866,820, a defect detection system for an EMAT inspection system to identify surface defects and sub-surface defects by using Lamb waves. The system does not show the features of the instant system and therefore could not be used in the same manner.

Thompson et al in U.S. Pat. No. 4,184,374, shows a ultrasonic inspection system for inspecting cylindrical objects. A group of EMATS are placed adjacent the material so that the transducers scan the entire object as it is rotated. Again, this does not show segmented magnets and flexible coils.

U.S. Pat. No. 6,170,336 to Johnson shows an EMAT configuration for sensing vibrations in a cylindrical object and methods of using an EMAT to determine resonant frequencies and physical properties of cylindrical objects. This system is very different from the instant invention.

Cook, in U.S. Pat. No. 5,907,100, shows a method for detecting defects in piping which employs an EMAT with sensors using a chirp coil and pulse sender. This system is incapable of performing like the instant invention.

GENERAL DESCRIPTION OF THE INVENTION

The EMATs of the instant invention are designed to detect defects or to measure properties within metallic components such as rod, wire, bar and relatively small cylinders which are symmetric about the central axis of any of the components. Specifically, magnets are used to provide magnetic fields in the components are either symmetrical or asymmetrical about a central axis. Coils of electrical conductors are wound or wrapped around said components and excited with an alternating current to provide magnetic fields which are symmetric with respect to the axis. These magnetic and coil combinations generate Lamb wave modes which are either symmetric or asymmetric with respect to the central axis of the components. These symmetric Lamb wave modes exhibit acoustic reflections of greater amplitude from defects on the central axis compared with reflections from defects which are located on the surface of said products. Detection of defects which are located on or near the central axis of said components at high speeds has been costly and difficult in the past if not impossible by nondestructive systems. The EMAT described in this patent application provide a reliable, cost-effective method of detecting defects on the central axis of said products at through-put speeds in excess of one meter per second. This provides for inspection of rolled and extruded products with EMATS which are in line with the fabrication process.

This nondestructive test facilities the removal of defective portions of the copper rod prior to drawing and finishing of the wire. This not only assures a high quality finished wire but also can provide substantial cost savings in labor and energy by diverting defective rod from further processing. Furthermore, the detection of defects during fabrication of the rod can provide additional savings by reducing the number of failures and resultant production down time during subsequent wire drawing process The utility and application of the EMAT described herein is further enhanced by the use of segmented magnets and flexible coils which retract from the center to provide a larger opening for passage of the leading end of a product as it exits from the production line at high speeds. After the leading end passes through the expanded opening the segmented EMAT will close around the product and inspection will commence. This closing prevents damage or destruction of the EMAT as well as minimizing the risk of stopping production or injury to production facility personnel.

OBJECTS OF THE INVENTION

It is an object of this invention to provide an improved EMAT inspection system for rods, wires and relatively small diameter metallic components, and It is a further object of this invention to provide an EMAT system whereby Lamb waves are used to inspect for defects and properties in small diameter metallic components, and A still further object of this invention is to provide for segmented magnets and flexible coils in an EMAT arrangement for measuring defects in metallic symmetrical objects, and Yet another object of this invention is to provide an EMAT system for measuring for properties and defects in a high-speed rotating environment, and These and other objects will become apparent when attention is turned to the accompanying drawings and specification.

DETAILED DESCRIPTION OF THE INVENTION

Figure 1:
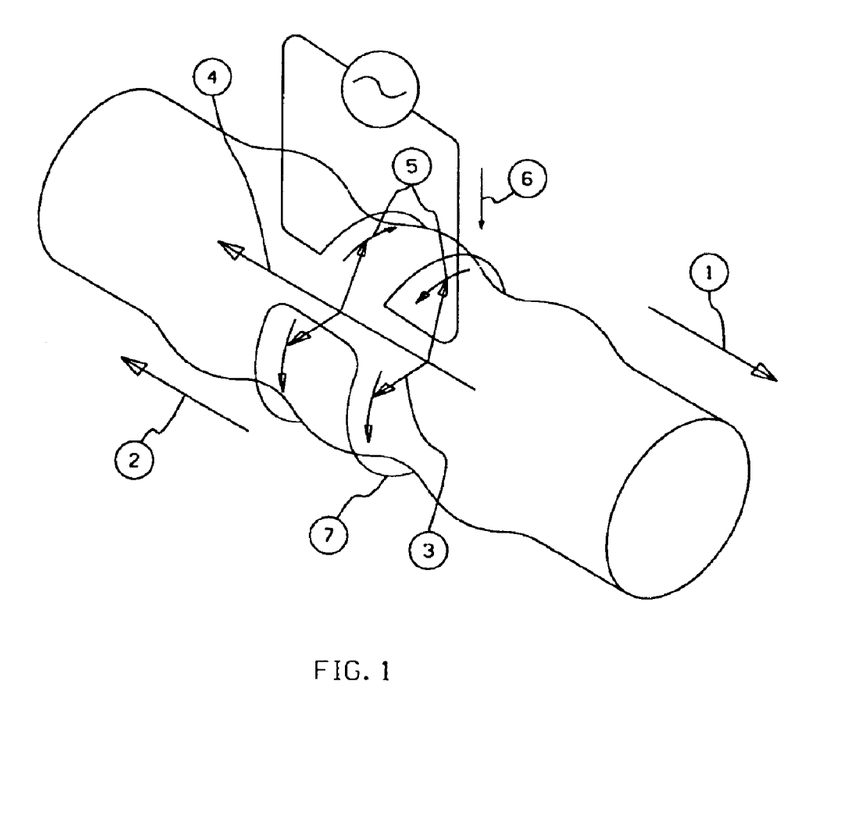
FIG. 1 illustrates the essential elements of an EMAT for generation of Lamb waves in a rod or tube of electrically conducting material

FIG. 1 illustrates the essential elements of the EMAT and the basic principles of the generation of Lamb waves in a rod or tubes of electrically conducting material. The acoustic waves 1 and 2 are produced by Lorentz forces generated by the EMAT at a fraction of a millimeter under the surface of the rod. The Lorentz forces 3 are generated by the interaction of a static magnetic field 4 from a magnetizing source such as a permanent magnet and eddy currents 5 induced by alternating currents 6 flowing through coils 7 of electrical conductors which encircle the rod. The eddy currents are induced by exciting the coils with an alternating current having a temporal frequency within the range of 50 KHz to 5 MHz. The excitation frequency is selected according to the desired acoustic wave mode, the acoustic properties of the rod or tube and the diameter of the rod or the wall thickness of the tube being inspected.

The eddy currents flow around the circumference of the rod at a location immediately under the windings of each encircling coil and in a direction parallel to the windings of the coil These eddy currents produce magnetic fields which either add or subtract to the magnetic bias field of the permanent magnet. When the current flows in a direction so as to generate magnetic fields which add to the static magnet field, the radial Lorentz forces are increased. Likewise, when the eddy current fields flow in a direction so as to generate a magnetic field which subtracts from the static magnet field, the radial Lorentz forces are decreased. This variation in the Lorentz forces produces Lamb waves which propagate away from the coils and down the length of the rod in two directions.

The amplitude of the acoustic shear wave is increased substantially by the addition of encircling coils as they are excited by electrical currents of the same frequency. Adjacent coils are wound in the opposite direction, i.e., one in the clockwise direction and the other in the counter clockwise direction. The coils are separated at a distance equal to half of a wave length of the acoustic Lamb wave generated in the rod. The frequency of the excitation current is adjusted electronically so that the radial Lorentz forces of adjacent coils are at maximum when the transmitted wave has traveled a distance along the rod equal to half a wavelength of the Lamb wave. Therefore, the acoustic wave transmission from each coil is increased in amplitude by the acoustic transmission from all of the other coils until a maximum amplitude occurs. The amplitude of the acoustic wave is maintained at a maximum until the electrical excitation current is removed or caused to decrease to zero. The acoustic wave decays to zero after the electrical excitation is removed in a manner which is similar to its ascent to maximum.

Figure 2:
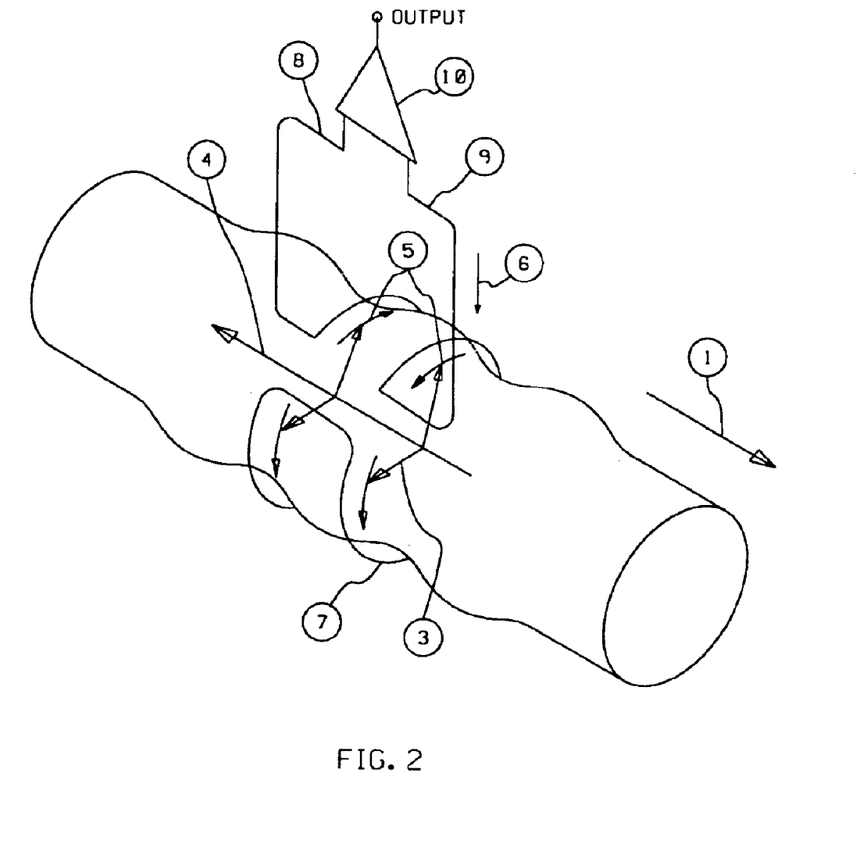
FIG. 2 illustrates the essential elements of an EMAT for detection of Lamb waves in a rod or tube of electrically conducting material.

Detection of the Lamb waves is essentially the reverse process of transmission. Illustrated in FIG. 2 is the detection of either the transmitted or reflected Lamb waves. The Lamb waves 1 can be detected by either a separate set of EMAT coils 7 or by the coils which are used to transmit the Lamb wave. In both of these cases, the coils are subjected to the relatively static field from either a permanent magnet or electromagnet. When a Lamb wave 1 passes under the detector coils, the rod expands and contracts at the temporal frequency of the Lamb wave. This vibration of the rod in the presence of the magnetic bias induces eddy currents 5 which flow in a direction that is parallel to the windings of the detector coils The eddy currents in turn induce a voltage which can be detected or measured at terminals of each coil. The coils are connected in series so that the induced voltages are added to provide a maximum signal voltage at the terminals 8 and 9 of the connected coils. This signal voltage can be detected by electronic amplifier 10 and transmitted to other system electronics for additional signal processing.

Figure 3:
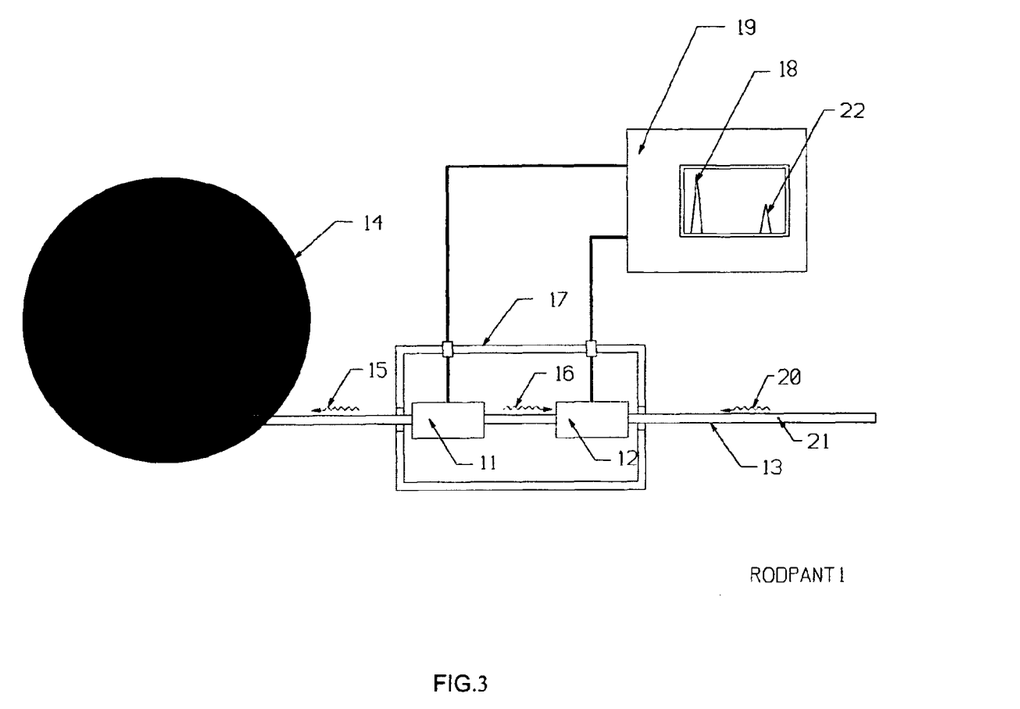
FIG. 3 is a diagram of an EMAT system being used for inspection of copper rods which illustrates a path traveled by the guided acoustic waves.

FIG. 3 shows an EMAT having a guided wave configuration being used for inspection of a solid cylindrical rod. Shown are two EMATs, a transmitter EMAT 11 and a receiver EMAT 12, housing 17 and the rod 13 being pulled through each EMAT and coiled on the other side of the EMATs into a large spool 14. Guided waves 15 and 16 are generated by the transmitter EMAT 11. The guided wave 16 is detected by the receiver EMAT 12 and results in an electrical signal response 18 displayed by the EMAT instrumentation 9. The guided wave 16 then continues to propagate toward the defect 21. Part of the wave 20 reflects from the defect and propagates back toward the receiver 12 where it is detected and results in a signal response 22 displayed by the EMAT instrumentation.

Figure 4:
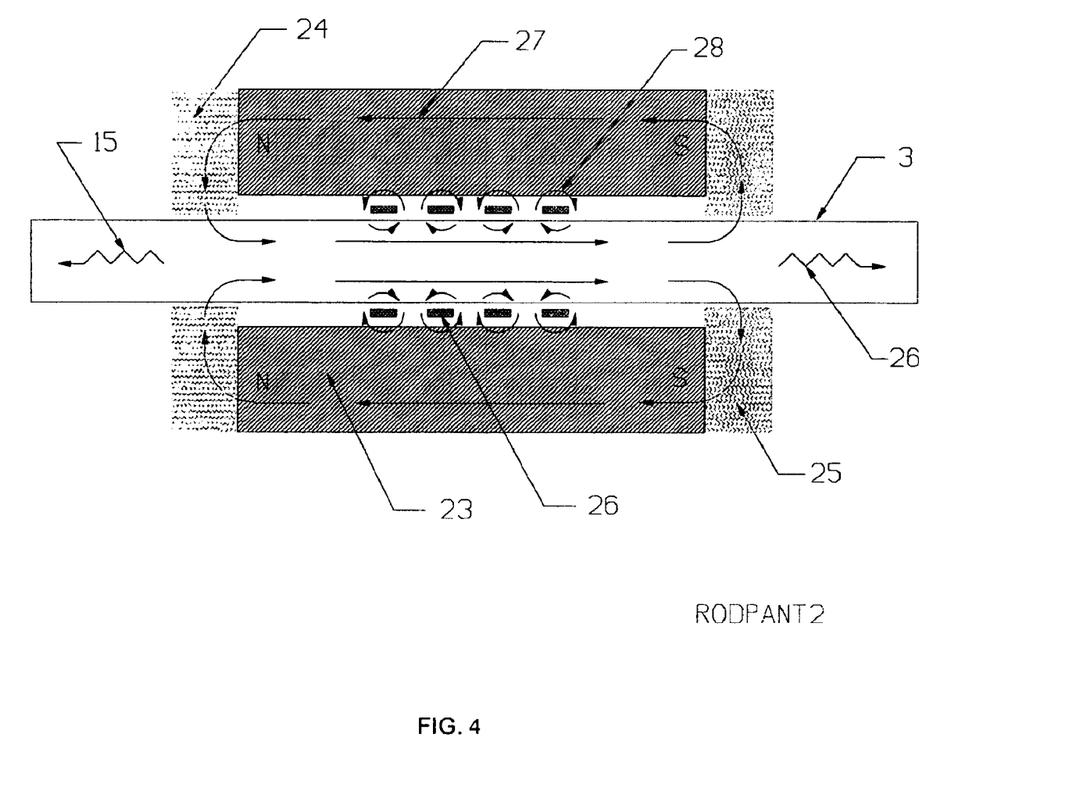
FIG. 4 shows a cross-section of an EMAT for generation and detection of symmetrical guided wave metal rods and shows a permanent magnet, a set of coils and the magnetic field induced in a rod by these components.

Referring now to FIG. 4 there is shown a cross-section of an EMAT, either a receiver or transmitter. The EMAT is composed of a magnet 23, pole pieces 24 and 25, and sets of coils 26 which encircle the rod. The coils for both the transmitter EMAT and the receiver EMAT are separated by equal distances between adjacent coils. The coils are wound with alternating polarity, i.e., clockwise, then counter clockwise, then clockwise, etc. and then are electrically connected in series. A static field 27 which is symmetrical with respect to the central axis of the EMAT and rod is induced by the magnet in the rod section which is closest to the bore of the magnet. The pole pieces 24 and 25 are composed of a hardened, ferromagnetic material such as carbon steel to provide the dual function of guiding the magnetic field into the rod and protecting the set of coils from wear and damage. The alternating currents produce alternating magnetic fields 28 around each coil. Interaction of these alternating magnetic fields with the static fields to produce Lamb waves 15 and 16 which propagate in both directions along the length of the rod.

Figure 5:
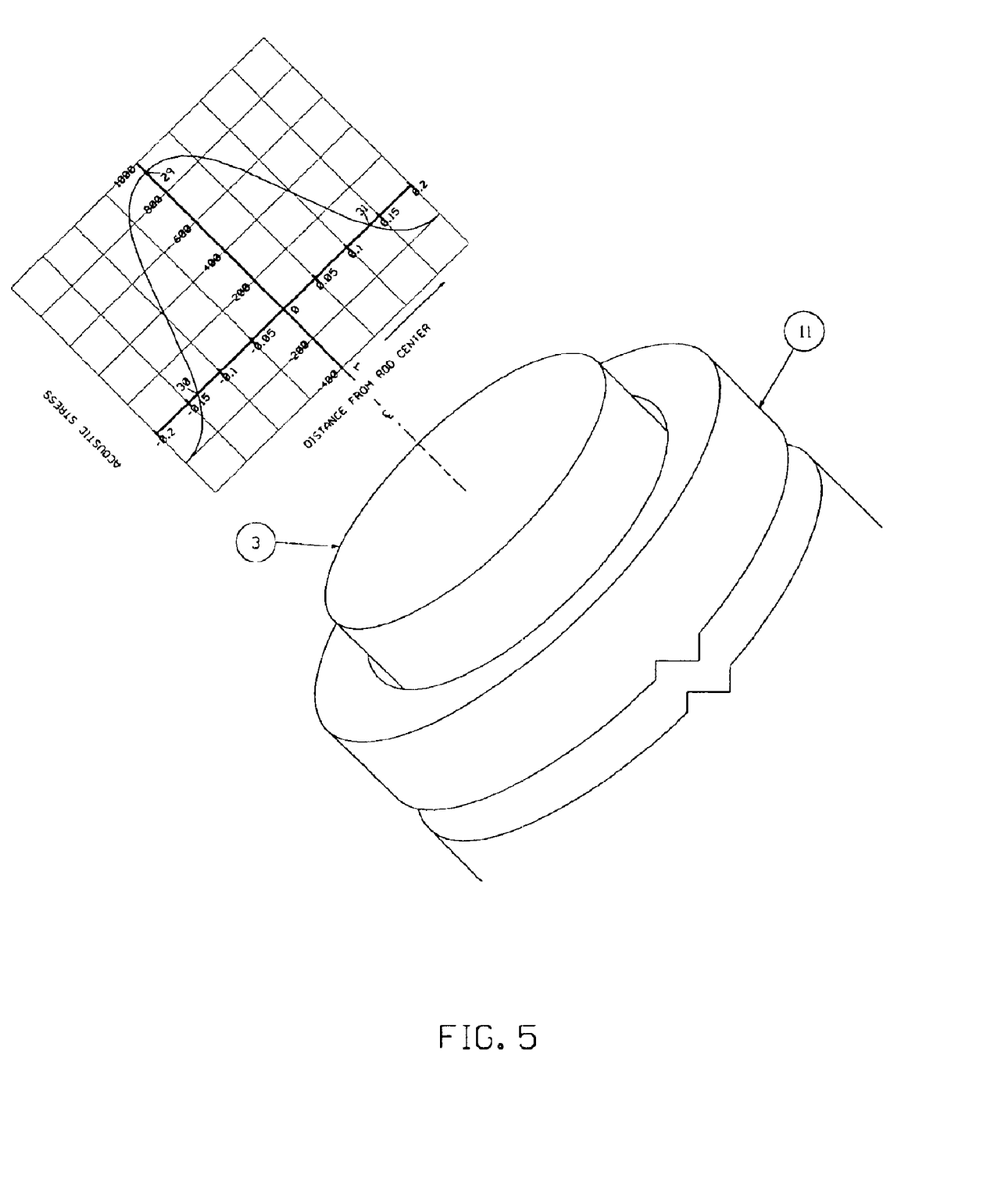
FIG. 5 illustrates the peak amplitude of the alternating stress distribution of the second order symmetrical Lamb wave mode.

The interaction of the symmetrical, static, magnetic field 27 with the induced alternating magnetic field 28 results in a Lamb wave which has a dynamic acoustic stress that is as a function of the radial distance from the center of the rod. Referring to FIG. 5, the peak amplitude in time of the alternating stress distribution of the second order symmetrical mode reaches a maximum acoustic stress 29 at the center of the rod and minimum stress 30 and 31 at the surface of the rod. This symmetric wave mode produces relatively large amplitude acoustic reflections from defects located at or nearer the surface of the rod as compared to acoustic reflections from defects located near the surface of the rod.

Figure 6:
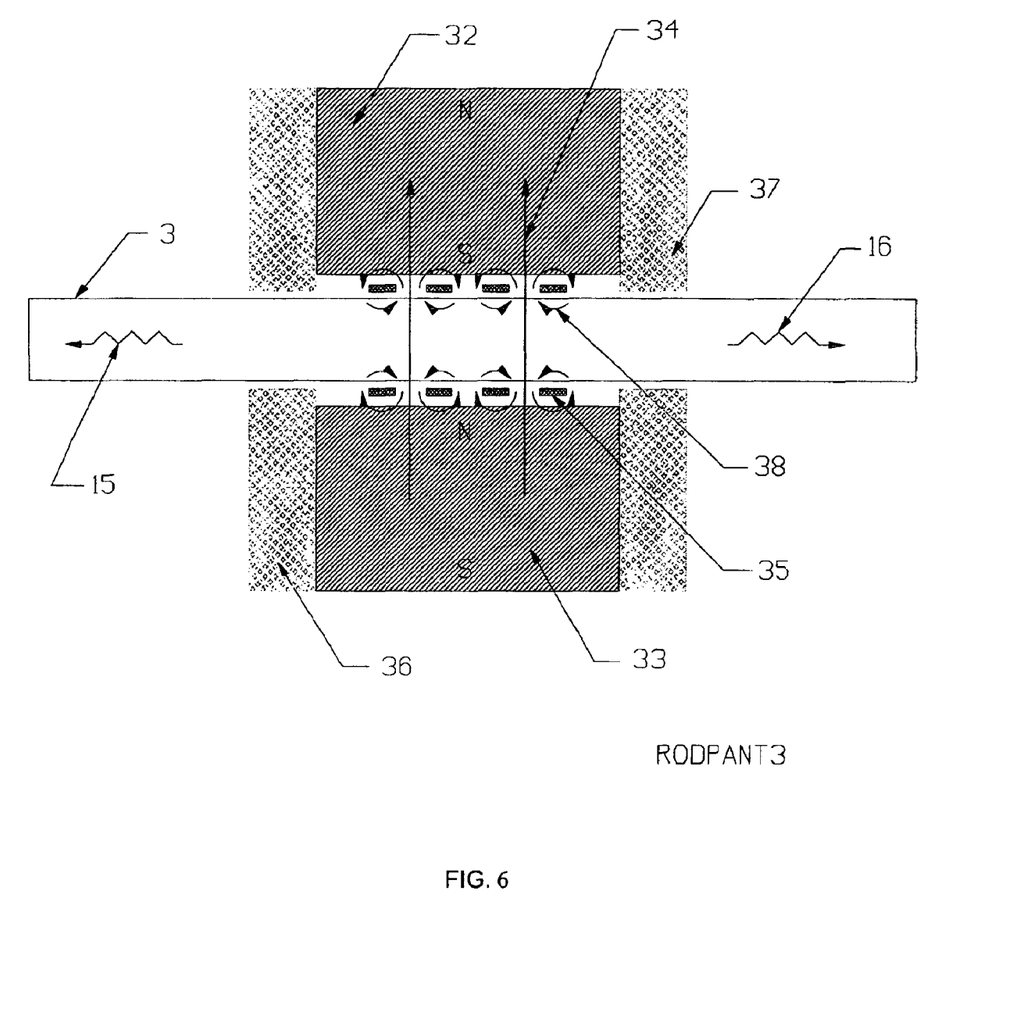
FIG. 6 shows a cross-sectional view of an EMAT for generation and detection of asymmetrical guided waves in metal rods and shows a permanent magent, a set of coils and the magnetic fields induced thereby.
Figure 7:
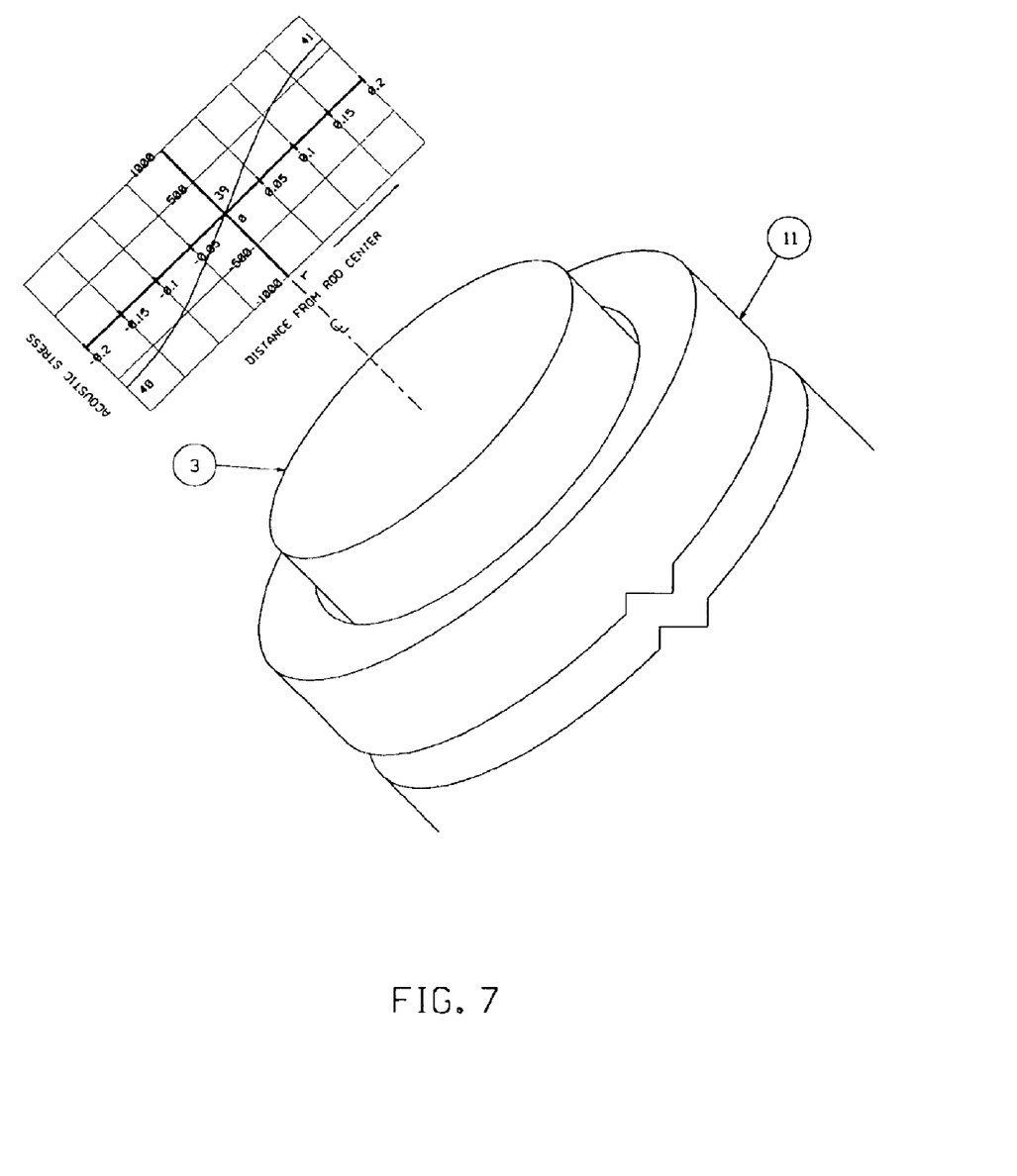
FIG. 7 illustrates the peak amplitude of the alternating stress distribution of the first order asymmetrical Lamb wave mode.

FIG. 6 illustrates an EMAT which produces guided waves asymmetrical about the central axis of a rod. As shown, magnets 32 and 33 generate a static magnetic field 34 which is perpendicular to rod 3 and the central axis of a set of coils 35. The end pieces 36 and 37 keep the rod 3 near the center of coils 35 and are composed of nonferromagnetic material to insure that the magnetic field 25 through the rod is maximized. The asymmetric static magnetic field interacts with alternating fields 38 from the coils and eddy currents to thereby generate guided wave modes which are asymmetric with respect to the central axis.

The interaction of the asymmetrical, static, magnetic field 34 with the induced alternating field 38 produces a Lamb wave which has a dynamic acoustic stress that is as a function of the radial distance from the center of the rod. Referring to FIG. 5, the peak amplitude in time of the alternating pressure distribution of the first order asymmetrical mode produces a minimum acoustic stress 39 at the center of the rod and a maximum stress 40 and 41 at the surface of the rod. This asymmetrical wave mode produces a greater acoustic stress at the surface of the rod, thereby providing relatively large amplitude acoustic reflections from defects located at or near the surface of the rod as compared to defects located near the center of the rod.

Referring to FIG. 3, the acoustic wave 16 which travels away from the spool 14 passes through a portion of the rod that is inside the receiver EMAT 12. Signal response 18 can be observed on left hand portion of the A—Scan Display 19.

The reflection 20 of the transmitted guided wave from defect 21 in the rod have a similar effect on the receiver EMAT 12. The amplitude of the reflected waves is smaller than the amplitude of the initial transmittedwave as indicated by the signal response 22 on the instrument display. As the reflectedwaves occur in time after the transmitted wave they are easily detected and identified by a gated data acquisition and signal processing instrumentation such as an oscilloscope or computer with an analog-to-digital converter. To inspect rods traveling at high speeds a pulse repetition rate of, say 500 Hz, and gate widths of sufficiently long duration to acquire and process the reflection signals are employed.

The commencement of a high-speed online inspection usually has the difficulty associated with it of threading the rod through the sensor without inflicting serious damage to the sensor and/or injury to personnel. If the attempt to pass the rod through the sensor is unsuccessful, substantial loss of production and revenue can result. This mechanical aspect is not affected by the acoustic waves and vice versa.

Figure 8:
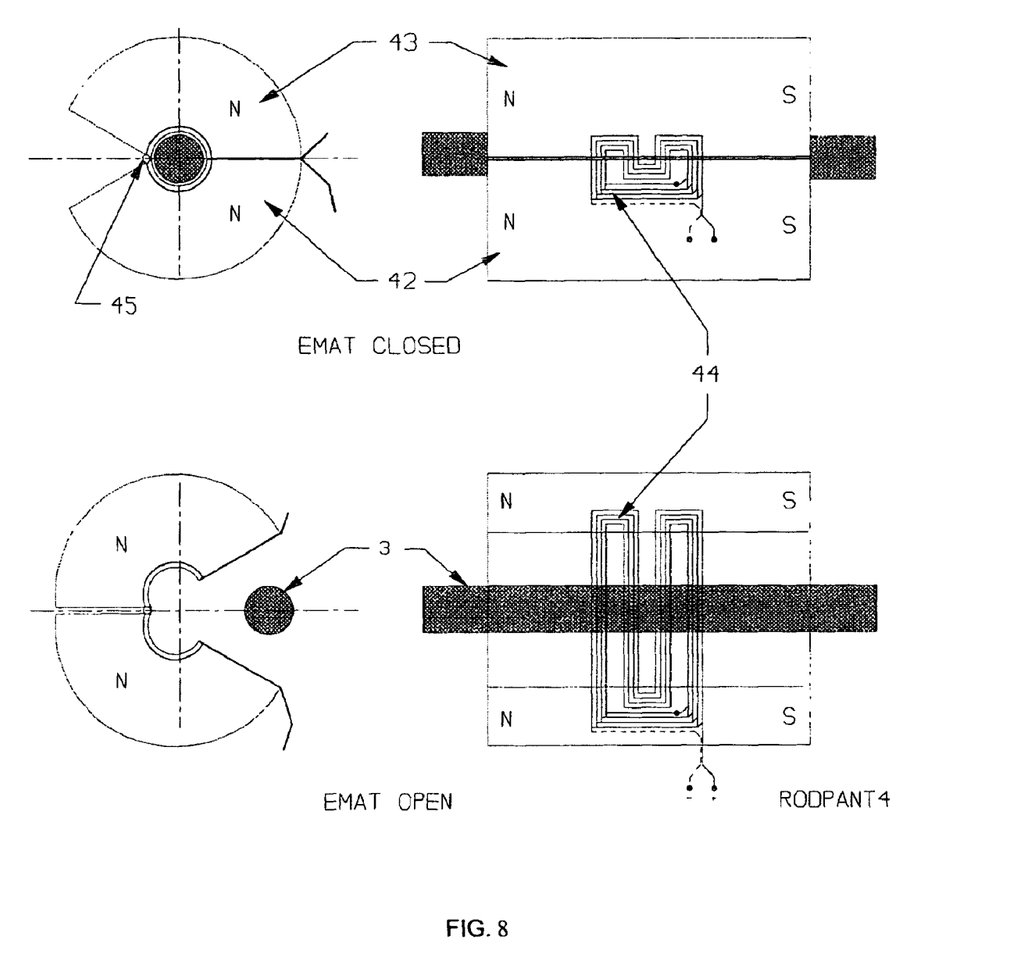
FIG. 8 shows a collapsible EMAT composed of segmental magnets and a flexible coil which can be opened during the start of an inspection for safe passage of the leading edge of a rod traveling at high speed.

FIG. 8 shows a collapsible EMAT composed of segmented magnets 42 and 43 and a flexible coil 44. The magnet sections are connected by a hinge 45 in this case so t that they can be rotated about the hinge to provide an opening sufficiently wide to facilitate removal of the EMAT from the region through which the end of the rod will pass. The flexible coil is attached to the internal surfaces of magnet sections so that it conforms to the contour of the magnet sections. Once the end of a rod passes through the open region and is stabilized, the open EMAT can be moved around the rod and closed to enable the magent sections and coil windings to form a sufficient magnetic coupling to perform the inspection.

Figure 9:
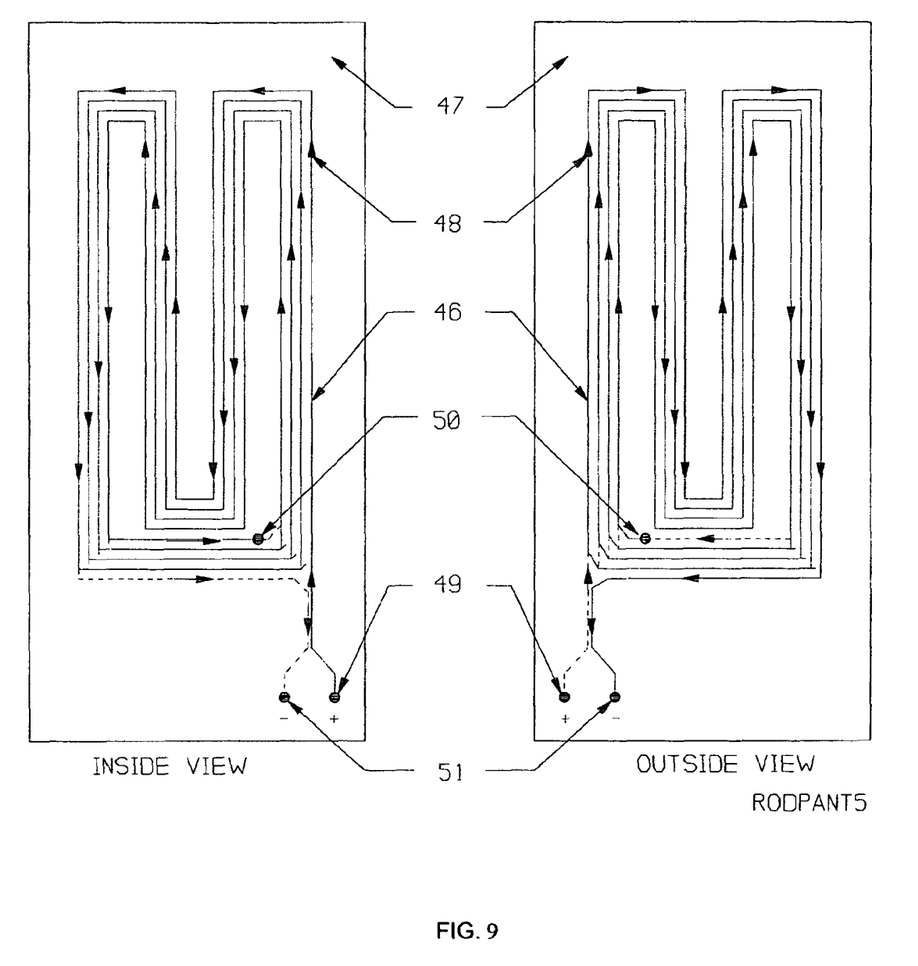
FIG. 9 is an illustration of a flexible coil which is attached to the internal surfaces of the magnet sections of a collapsible EMAT.

FIG. 9 shows a flexible coil which is attached to the interior of a magnet section. It is composed of electrical conductors 46 etched on a thin plate substrate 47 typical of the material used in the fabrication of printed circuits. The coil windings are covered with a thin sheet of the same material to insulate the electrical conductors and prevent electrical arcing or shorting to the rod. The inside view of the flexible coil, shown on the left hand side of FIG. 9, shows the continuous current 48 path when a voltage is applied to the terminals with the indicated polarity. The current flows from the positive terminal 49 along the conductor and passes through the via or electrical connection to the outside surface illustrated on the right hand side of FIG. 9 and then proceeds to flow from the via to the negative terminal 35.

Figure 10:
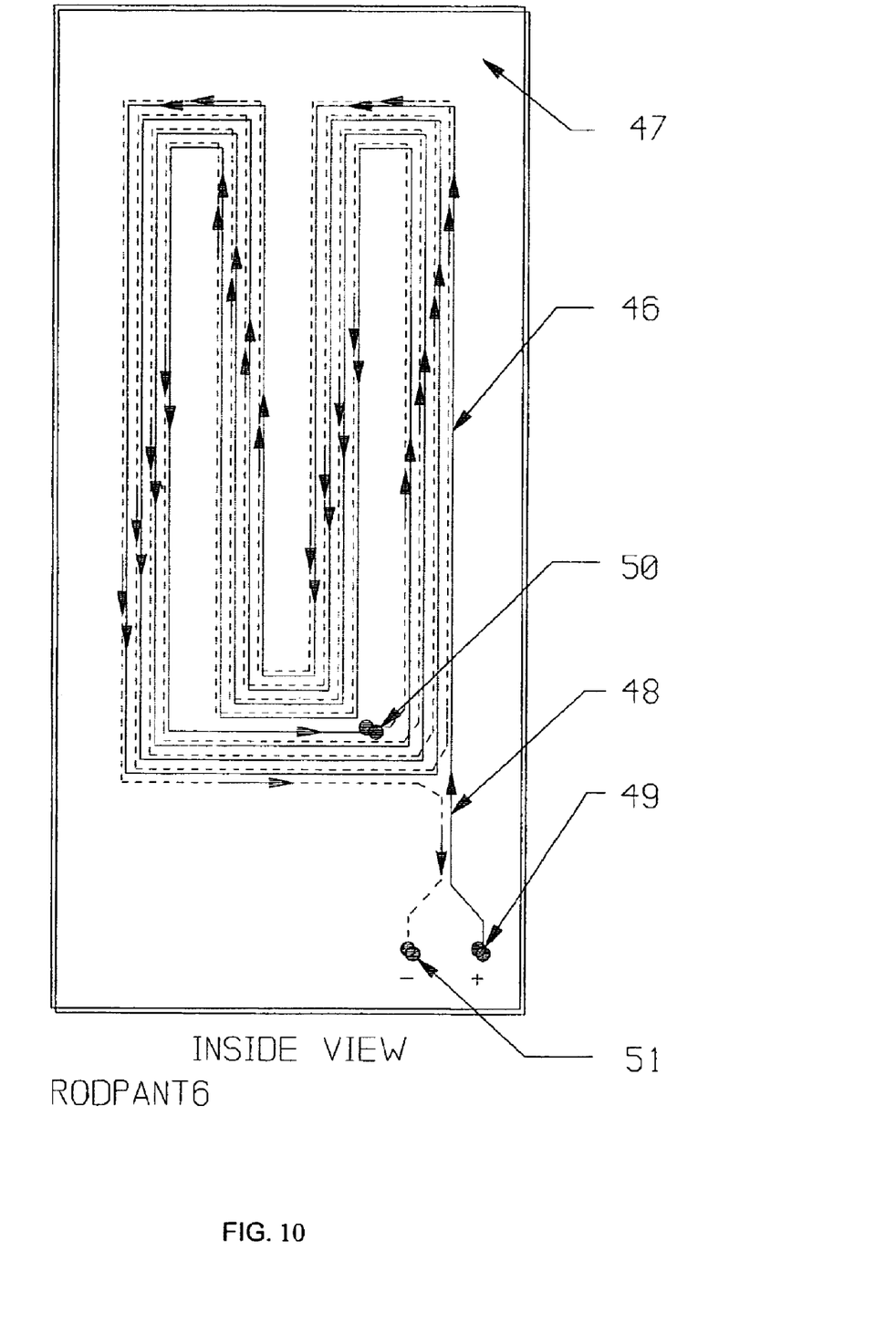
FIG. 10 illustrates the assembly of two—side flexible printed circuit coils for use with a collapsible EMAT.

FIG. 10 shows a perspective view of the double-sided flexible printed circuit assembly. During use of the EMAT electrical current 48 enters the positive terminal 49 and passes along the conductor 46 on the inside surface of flexible substrate 47 to via 50. The electrical current then passes through the via to the conductors on the outside surface of substrate 47 where it flows along the conductors in the same direction as the current flowing in the adjacent conductors on the inside surface of the substrate and into the negative terminal.

The flexible coil is designed so that the portions of it which are wrapped closely around the rod have overlaying conductors on the inside and outside surfaces of the flexible substrate. As the current flows in the same direction in adjacent conductors on each side of the substrate, the induced magnetic field increases by approximately a factor of two compared to the field induced by a coil that has conductors only on one side the substrate. This results in a corresponding increase in the eddy current density induced in the rod under each part of the flexible coil which is in close proximity to the rod. A similar, double sided receiver coil design provides approximately twice the signal voltage at the output terminal compared to a single sided coil design.

Having described some preferred embodiments of my invention, it will be obvious to those of ordinary skill in the art that many changes and modifications can be made without departing from the scope of the appended claims.

What is claimed:

1. A guided wave electromagnetic acoustic transducer for detection of defects and/or or variances in the physical properties of metallic products including rods, wires, bars and tubes, all having a central axis, transmitting and detecting acoustic waves in these products, said transducer comprising a housing means, electromagnetic means within said housing for establishing a static magnetic field in said metallic products being inspected, electrical conductors for wrapping around said metallic products to encircle the same for producing eddy currents in said products, said conductors being energized by a pulse of a few cycles of high frequency alternating voltage which produces an alternating field in said metallic products, which, in turn, produces eddy currents which flow around the circumference of the section of the metallic product being tested, and means for inducing said eddy currents in said electrical conductor to produce, by the interaction of said eddy currents and said static magnetic field, Lamb waves which propagate along said metallic products in two directions, and means for detection of said Lamb waves to allow said transducer to detect any defects or variances.

2. A transducer as in claim 1 wherein said electromagnetic means produces a symmetrical magnetic field with respect to the central axis of the products being tested.

3. A transducer as in claim 1 including a support structure encircling said metallic products, said electrical conductors being wrapped around said support structure so as to produce a symmetrical alternating magnetic field with respect to the central axis of said product when the conductors are excited by alternating electrical currents.

4. A transducer as in claim 3 wherein said support structure and electrical conductors are so positioned to enable the electrical fields to interact to produce acoustic stress waves which can propagate in a direction parallel to the central axis of said products to thereby afford an increased signal response to defects and properties located on and along the central axis of the products.

5. A transducer as in claim 3 wherein said electrical conductors comprise coils, said coils being flexibly mounted on said support structure to allow said conductors to adjustably accommodate various sized metallic structures by encircling them.

6. A transducer as in claim 1 wherein said electromagnetic means comprise segmented magnets.

7. A transducer as in claim 6 wherein said electromagnetic means are hinged to allow easy access for products being tested and wherein said magnetic means can be opened and closed upon the product being tested.

8. A transducer as in claim 1 wherein the Lamb waves can vary depending on the amount of excitation.

9. A transducer as in claim 1 wherein said eddy currents are produced by coils incorporated into said electrical conductors.

10. A transducer as in claim 1 wherein acoustic reflections of a large amplitude result when the static magnetic field is symmetric with respect to the central axis of the product.

11. A guided wave electromagnetic acoustic transducer for providing transmittal and receiving of acoustic waves to detect variations and/or defects in metallic products with a central axis, said transducer including at least one segmented magnet for movement to and away from the central axis of such a product so as to allow said magnet to closely encircle said product regardless of the diameter of said product and a set of coil means connected in series so that induced voltages are added to provide maximum signals for detection.

12. A transducer as in claim 11 and including at least one coil means flexibly mounted so as to adapt to the diameter of said products by moving away or closer to said product depending on the diameter thereof.

13. A guided wave electromagnetic transducer as in claim 11 and including two electromagnetic acoustic transducers, one for transmitting waves within said product and a second to receive the reflected waves; so as to detect variances or defects in said products.

14. A guided wave electromagnetic acoustic transducer for providing transmittal and receiving of acoustic waves to detect variations and/or defects in metallic products with a central axis, said transducer including
  at least one coil flexibly mounted so as to adapt to the diameter of said products by either moving toward or away from the axis of said product to encircle said product about its diameter,
  said coils having alternate windings so as to detect Lamb waves measuring the dynamic acoustic stress in said products that is a function of the radial distance from the center of said metallic product therefore producing a reading that interprets reflected waves from a surface defect as smaller than those waves reflected from the center of the metallic product.

15. A transducer as in claim 14 at least one segmented magnetic means hingedly adapted to encircle the diameter of any such product to cooperate with said coils to transmit and receive Lamb waves.

16. An EMAT to detect defects both along the surface and at the center of various metallic products including rods, tubes, wires and bars, all having a central axis, by transmitting acoustic waves in these products, said EMAT comprising,
  housing means
  means to generate a static magnetic field in said products,
  means to generate eddy currents in said products to generate, in conjunction with said static magnetic field, Lamb waves along the length of said products, and
  means to detect said Lamb waves to ascertain the existence of defects either along the surface or in the center of said products, said means for detecting said Lamb waves measuring the dynamic acoustic stress that is a function of the radial distance from the center of the metallic product thus producing a reading that interprets reflected waves from surface defects as smaller than reflected waves from the center of said products.

17. An EMAT as in claim 16 wherein said means for generating a static magnetic field is a permanent magnet.

18. An EMAT as in claim 16 wherein said means for generating eddy currents in said products is a series of coils encircling the axis area of said products.

19. An EMAT as in claim 18 wherein said coils are alternately wound, clockwise and counterclockwise and then separated by a distance equal to one half of the acoustic Lamb wave generated by the interaction of said eddy currents and said static magnetic field.

20. An EMAT as in claim 16 wherein the means to induce eddy currents in said metallic products produces a frequency from 50 KHz to 5 MHz, the excitation frequency selected depending on the acoustic wave mode, the acoustic properties of the metallic product and the diameter or wall thickness of the metallic product.

21. An EMAT as in claim 20 wherein the variation in excitation to the metallic product causes increases and/or decreases in the radial Lorentz forces thus producing the Lamb waves which can be detected for defects in the products.

22. An EMAT as in claim 21 wherein the variation said means for inducing the eddy currents comprises a series of coils surrounding said metallic products and being alternately wound and connected in series.

23. An EMAT as in claim 22 wherein the excitation current is adjusted so that the radial Lorentz forces of adjacent coils are at a maximum when the transmitted wave has traveled a distance equal to one half of the wave length.

24. An EMAT as in claim 16 wherein said means for detecting the strength of said Lamb waves comprise a set of coils connected in series so that induced voltages are added to provide maximum signals for detection.

25. An EMAT as in claim 24 wherein said guided acoustic Lamb wave travels along the length of said metallic product until it encounters a defect and then is reflected back to said coils where it is detected by an electronic amplifier.

26. An EMAT as in claim 16 wherein said means for detecting said Lamb waves comprises a series of coils surrounded by a permanent magnet which produces a magnetic field perpendicular to the eddy currents in said metallic product, thus producing a voltage which can be detected and measured.

27. An EMAT as in claim 26 wherein said magnet includes two pole pieces which protect the coils from wear and guide the metallic product through the EMAT.

28. An EMAT as in claim 27 wherein said magnet includes two pole pieces which are made of nonferromagnetic material.

29. An EMAT as in claim 16 wherein the means for producing a static magnetic field is a hinged permanent magnet and the means for producing eddy currents are a flexible coil attached to the internal sections of said magnet.

30. An EMAT as in claim 29 wherein the flexible coil comprises electrical conductors etched on a thin plate substrate and covered by a second thin substrate.

31. An EMAT as in claim 30 wherein there is a via in said coil dividing it into a length along the outside of the surface of said magnet and another length along the inside of said magnet, thus increasing, by approximately, a factor of five, the induced magnetic field.

32. The method of detecting defects in metallic products including pipes, rods, bars and wires, said method comprising,
  providing a static magnetic field along said metallic product,
  providing excitation by a pulse of a few cycles of high frequency alternating voltage to produce an alternating field in said product, to provide eddy currents along the length of said product and around the circumference of said product to interact with said static magnet field to produce Lorentz forces,
  monitoring the Lamb waves created by the interaction and reflection off of defects along the length of said product so as to locate the defect by signal strength.

33. A method as in claim 32 and including the step of adjusting the frequency of said excitation so that the radial Lorentz forces are at a maximum.

34. A method as in claim 32 wherein the step of creating the static magnetic field and said excitation of eddy currents is performed by an EMAT.

35. A method as in claim 32 wherein the step of monitoring said Lamb waves is performed by an EMAT.

36. A hinged EMAT for testing for defects along the length of installed wires, bars, rods, or tubing and other metallic products where the product is already installed and cannot be removed, said EMAT including:
  a hinged permanent magnet adapted to open and close around a length of said product and produce a magnetic field therealong, and
  coil means along the surface of said magnet which encircles said product so as to provide eddy currents to interact with said magnetic field so as to produce measurable Lamb waves for detection of defects in said product, and
  said permanent magnet surrounding said coil means and including two pole pieces which protect said coil means from wear and guide the EMAT along the metallic product.

* * * * *